United States Patent [19]

Benedict

[11] 4,110,083

[45] Aug. 29, 1978

[54] ABRASIVE COMPOSITION

[75] Inventor: James John Benedict, Cincinnati, Ohio

[73] Assignee: The Procter & Gamble Company, Cincinnati, Ohio

[21] Appl. No.: 677,592

[22] Filed: Apr. 16, 1976

Related U.S. Application Data

[63] Continuation of Ser. No. 471,941, May 21, 1974, abandoned.

[51] Int. Cl.$^2$ .......................... A61K 7/16; B24D 3/30
[52] U.S. Cl. ................... 51/295; 51/298 R; 424/49; 424/54; 427/220; 427/221
[58] Field of Search ............... 51/295, 298; 424/54, 424/49; 427/220, 221

[56] References Cited

U.S. PATENT DOCUMENTS

| | | | |
|---|---|---|---|
| 3,151,027 | 9/1964 | Cooley et al. | 424/54 |
| 3,591,675 | 7/1971 | Brilliant | 424/54 |
| 3,624,120 | 11/1971 | Yetter | 424/54 |
| 3,703,583 | 11/1972 | Martin | 424/54 |
| 3,749,767 | 7/1973 | Bauman | 424/54 |
| 3,804,946 | 4/1974 | Harrison | 424/54 |
| 3,955,942 | 5/1976 | Cordon et al. | 51/295 |

*Primary Examiner*—Donald J. Arnold
*Attorney, Agent, or Firm*—Douglas C. Mohl; Leonard Williamson; Richard C. Witte

[57] ABSTRACT

A dentifrice abrasive coated with a cationic water-soluble polymer which abrasive is thereby made less adsorptive to therapeutic cationic agents, and therapeutic compositions containing said abrasive.

7 Claims, No Drawings

ABRASIVE COMPOSITION

CROSS REFERENCE TO RELATED APPLICATION

This application is a continuation of the application of James J. Benedict having Ser. No. 471,941, filed May 21, 1974 now abandoned.

FIELD OF THE INVENTION

This invention relates to a coated dentifrice abrasive consisting of a hard mineral substance coated with a water-soluble cationic polymer and to dentifrice compositions containing such coated abrasive.

BACKGROUND OF THE INVENTION

A satisfactory dentifrice should have a cosmetic effect on teeth, keeping them light colored. It should also have a functional effect on the teeth and mouth, keeping them clean and free from food debris, thereby aiding prevention of tooth decay and promoting gingival health. In order to achieve these objectives, it is necessary to brush with a dentifrice containing an abrasive. The purpose of the abrasive is to aid in removal of the tightly adherent film which, in many persons, contains pigments which color it brown or yellow. The abrasive should remove this film, called the pellicle film, with a minimum abrasion of the underlying tooth material. Enamel, which covers much of the exposed tooth surface, is relatively hard and is not of as much concern as the softer dentin which may be exposed by receding gums.

Beyond the function of a dentifrice in maintaining oral cleanliness, there is merit in including an agent which acts specifically to reduce tooth decay or counteract diseases affecting the gingiva. Work stimulated by the discovery of the beneficial effect of fluoride in drinking water or topically applied to the teeth has led to the development of dentifrices containing water-soluble fluorides. The effect of stannous fluoride in a properly formulated dentifrice in reducing caries has been well established. Other inorganic fluorides such as indium fluoride have also been shown to be effective anticaries agents. It has also been found that bis-biguanide compounds such as those disclosed in U.S. Pat. No. 2,684,924, Rose et al., July 27, 1954, are effective antiplaque agents which demonstrate anticaries activity.

A problem recognized in the scientific and patent literature is that of formulating a dentifrice in which the ionic therapeutic agents will remain available for treatment of the teeth and not react with the abrasive.

It is an object of this invention to provide an abrasive coated with a water-soluble cationic polymer which improves the compatibility of the abrasive with cationic therapeutic agents, thereby allowing more of the agent to remain available for therapeutic treatment of the tooth surface.

It is a further object of this invention to provide a preferred dentifrice containing the cationic polymer coated abrasive and a cationic therapeutic agent.

PRIOR ART

U.S. Pat. No. 3,151,027, Sept. 29, 1964 to Cooley et al., discloses dentifrice abrasives which are hard mineral substances such as silica coated with a substantially water-impervious, cross-linked, thermosetting, highly polymerized resin. Suitable types of synthetic resins are disclosed to be melamines, phenolics, ureas, melamine ureas, cross-linked epoxies and cross-linked polyesters. The purpose of the coating is disclosed as being to improve the ionic compatibility of the abrasives. However, this reference does not disclose the cationic polymer coatings of the present invention.

U.S. Pat. No. 3,703,583, Nov. 21, 1972 to Martin, discloses dentifrices containing silica abrasives and anticalculus agents which are quaternary ammonium compounds. This reference similarly does not disclose the cationic polymers of the present invention nor the cationic therapeutic agents of the present invention.

SUMMARY OF THE INVENTION

The present invention relates to dentifrice abrasives which have been coated with a water-soluble cationic polymer and to aqueous therapeutic compositions containing the coated abrasive. The coated abrasive has improved compatibility with cationic agents so that less therapeutic agent is adsorbed by the abrasive and more is available for treatment of the teeth.

DETAILED DESCRIPTION OF THE INVENTION

The abrasives suitable for use in this invention are generally hard inorganic mineral substances. The substance should have a hardness on a Mohs' scale of not less than 2 to insure that the abrasive adequately cleans the teeth after being coated with the polymer. The average particle size of the substance should be substantially in the range of about 1 micron to about 30 microns. Smaller sizes do not result in effective cleaning agents. Larger sizes, particularly after being coated, tend to feel gritty in the mouth.

Examples of hard mineral (or mineral-like) substances useful as abrasives in this invention are silica, calcium silicate, silicon carbide, pumice, alumina, ilmenite, hematite, zirconium silicate, calcium pyrophosphate, calcium carbonate, tricalcium phosphate, insoluble metaphosphate, and dicalcium orthophosphate. Silica is a preferred hard mineral substance of this invention.

A preferred silica is amorphous silica, including silica gels, nonporous precipitates, and pyrogenic materials, which can be considered polycondensation products of orthosilicic acid $Si(OH)_4$. The physical structure of amorphous silica is represented by a system of polycondensation units or primary particles, the size and packing of which determine the exact geometry of the structure. This structure, as defined by surface area, pore volume, and pore size, depends on the size and degree of packing of the elementary or ultimate particles. The latter consist of dimensional networks of $SiO_4$ tetrahedra. The only difference between gels and precipitates is the degree in strength of packing and the silica aggregates.

Amorphous silica abrasives suitable for use in the present invention must have cleansing ability and be safe for use in the oral cavity. Cleansing ability depends on the interrelated factors of hardness, particle size, shape, and structure. Safety requires that these be such that the abrasives can penetrate and remove stain and debris from and around the tooth without scratching or otherwise harming the enamel surface of the tooth, the tooth's dentin, or the adjacent soft tissues under normal conditions of toothbrushing. The literature has disclosed the use of various natural and synthetic silicas as abrasives and polishing agents in various compositions including dentifrices, either alone or in combination with other polishing agents. See, for example, German Pat. No. 974,958; French Pat. No. 1,130,627; British Pat. No. 995,351; Swiss Pat. No. 280,671; and the following U.S. Patents: Menkart et al, U.S. Pat. No. 3,250,680; issued May 10, 1966; Pader et al., U.S. Pat. No. 3,538,230, issued Nov. 3, 1970; Wiesner et al., U.S. Pat. No. 3,662,059, issued May 9, 1972 and Pader, U.S. Pat. No. 3,689,637, issued Sept. 5, 1972.

Preferred amorphous silica abrasives for use in the present invention are synthetic, amorphous, porous silica xerogels having an average particle size of from 1 to about 30 microns.

Examples of preferred xerogel abrasives which are commercially available are the materials sold by W. R. Grace & Co., Davison Chemical Division, under the names Syloid 63, Syloid 65, Syloid 72 (including grades 72, 73 and 79), Syloid 74, Syloid 75, Syloid 620, Syloid 244 and Syloid 621. These materials are defined in a brochure of Davison entitled "DAVISON FAMILY OF SYLOID® SILICAS AT WORK", pp. 59–71, incorporated herein by reference.

Syloid 63 has a particle size of about 9 microns, a surface area of about 675 $m^2$/gm., oil absorption of about 60 lb./100 lb., a bulk density of about 29 lb./$ft.^3$, a silica particle density of about 1.05 gms/c.c., and an average pore diameter of about 25 Angstroms.

Syloid 65 has a particle size of about 4.5 microns, a surface area of about 695 $m^2$/cm., oil absorption of about 75 lb./100 lb., a bulk density of about 23 lb./$ft.^3$, a silica particle density of about 1.05 gms/c.c., and an average pore diameter of about 25 Angstroms.

Syloid 72, grade 72, has a particle size of about 4 microns, a surface area of about 340 $m^2$/gm., oil absorption of about 220 lb./100 lb., a bulk density of about 11 lb./$ft.^3$, a silica particle density of about .65 gms/c.c., and an average pore diameter of about 150 Angstroms.

Syloid 72, grade 73, has a particle size of about 4 microns, a surface area of about 330 $m^2$/gm., oil absorption of about 200 lb./100 lb., a bulk density of about 9 lb./$ft.^3$, a silica particle density of about 0.65 gms/c.c., and an average pore diameter of about 150 Angstroms.

Syloid 72, grade 79, has a particle size of about 4 microns, a surface area of about 340 $m^2$/gm., oil absorption of about 220 lb./100 lb., a bulk density of about 11 lb./$ft.^3$, a silica particle density of about 0.65 gms/c.c., and an average pore diameter of about 150 Angstroms.

Syloid 74 has a particle size of about 8 microns, a surface area of about 320 $m^2$/gm., oil absorption of about 200 lb./100 lb., a bulk density of about 16 lb./$ft.^3$, a silica particle density of about 0.65 gms/c.c., and an average pore diameter of about 150 Angstroms.

Syloid 75 has a particle size of about 2.6 microns, a surface area of about 360 $m^2$/gm., oil absorption of about 215 lb./100 lb., a bulk density of about 10 lb./$ft.^3$, a silica particle density of about 0.65 gms/c.c., and an average pore diameter of about 150 Angstroms.

Syloid 620 has a particle size of about 20 microns, a surface area of about 320 $m^2$/gm., oil absorption of about 180 lb./100 lb., a bulk density of about 21 lb./$ft.^3$, a silica particle density of about 0.65 gms/c.c., and an average pore diameter of about 150 Angstroms.

Syloid 621 has a particle size of about 25 microns, a surface area of about 320 $m^2$/gm., oil absorption of about 180 lb./100 lb., a bulk density of about 23 lb./$ft.^3$, a silica particle density of about 0.65 gms/c.c., and an average pore diameter of about 150 Angstroms.

Most preferred xerogels are those having densities greater than about 1 gm/c.c. and surface areas of greater than about 600 $m^2$/cm. The cleaning ability of these particles is much greater than the cleaning ability of those xerogels having densities of about 0.65 gms/c.c. and surface areas of closer to 300 $m^2$/gm. Howwever, the lower density abrasives have much lower RDA (Radioactive Dentin Abrasion) values and thus damage to the tooth is minimized. In general, higher RDA values are associated with better cleaning. Mixtures of 1 gm/c.c. density and 0.65 gm/c.c. density xerogel abrasives are desirable from the standpoint of arriving at a compromise position for cleaning while maintaining acceptable physical properties for the compositions.

Also preferred amorphous silica abrasives are precipitated amorphous silica abrasives such as those supplied by the J. M. Huber Corporation undder the names Zeosyl, Zeo and Zeolex.

The coated abrasives of the present invention are made by coating an abrasive which is a hard mineral substance with a cationic water-soluble polymer, wherein the polymer has a molecular weight of from about 500 to about 1,000,000, and has a cationic charge density of at least 0.003, and is generally in the range from about 0.003 to about 0.015 in aqueous solution.

The "cationic charge density" of a polymer as that term is used herein refers to the ratio of the number of positive charges on a monomeric unit of which the polymer is comprised to the molecular weight of said monomeric unit, i.e., $$\text{cationic charge density} = \frac{\text{number of positive charges per monomer}}{\text{monomeric unit molecular weight}}$$

The cationic charge density multiplied by the polymer molecular weight determines the number of positively charged active sites on a given polymer chain.

The water-soluble cationic polymers of the present invention can be any water-soluble cationic polymer suitable for use in dentifrice products, and which meets the aforementioned criteria. The preferred polymers, however, are nitrogen containing. These may be amines or quaternary ammonium compounds with the latter being preferred due to their charge being independent of pH. Examples of the quaternary ammonium polymers are the following structures:

1. Polyacryloxyalkyl ammonium or polymethacryloxyalkyl ammonium salt (e.g., the quaternary ammonium salt of dimethylamino ethyl methacrylate, polymerized);
2. Polyacryloamido alkyl ammonium salt (e.g., the quaternary ammonium salt of dimethylamino ethyl methacrylamide, polymerized);
3. Polyalkenyl ammonium salt (e.g., the quaternary ammonium salt of vinyl chloroacetate, polymerized);
4. Polyvinyloxyalkyl ammonium salt (e.g., the quaternary ammonium salt of vinyl ethoxy dimethylamino, polymerized);
5. Polyvinylbenzyl ammonium salt (e.g., the quaternary ammonium salt of chloromethyl styrene, polymerized);
6. Polydiallyl ammonium salt (e.g., the quaternary ammonium salt of dimethylamino diallyl, polymerized);
7. Polyvinyl pyridinium ammonium salt (e.g., the quaternary ammonium salt of vinyl pyridine, polymerized);
8. Polyvinylimidazolinium salt (e.g., the reaction product of 1-(β-dimethylamino ethyl)-3- vinylimidazolinone-2 and tetrahydropyrimidanone-2, polymerized);
9. Polyalkylation quaternaries (e.g., the reaction product of decamethylene dibromide and N,N,N',N'-tetramethylhexamethylene diamine, polymerized);
10. Polycondensation quaternaries (e.g., the quaternary ammonium salt formed by reacting polyepichlorohydrin with pyridine, polymerized).

Examples of preferred polymers are the following:

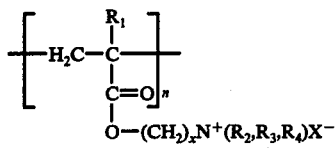
I where $n$ is the number of repeating monomeric groups and is selected so as to give a polymeric molecular weight of from 500 to 1,000,000, $R_1$ is either H or $CH_3$, $x$ is from 2 to about 5, $R_2$, $R_3$ and $R_4$ are the same or different alkyl radicals of from 1 to 4 carbon atoms or an aryl radical, and $X^-$ is a halide ion (e.g., fluorine, chlorine, bromine or iodine), or $HSO_4^-$ or $CH_3SO_4^-$,

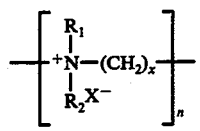
II where $x = 1 - 14$, $n$ is the number of repeating monomeric groups, and is selected so as to give a polymeric molecular weight of from 500 to 1,000,000, $R_1$ and $R_2$ are $CH_3$, and $X^-$ is a halide ion,

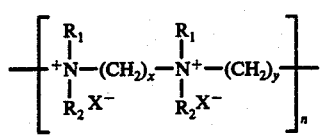
III where $x = 2-6$, $y = 3-20$, $n$ is the number of repeating monomeric groups and is selected so as to give a polymeric molecular weight of from 500 to 1,000,000, $R_1$ and $R_2$ are $CH_3$, and $X^-$ is a halide ion,

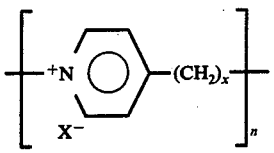
IV $x = 1-12$, $n$ is the number of repeating monomeric groups and is selected so as to give a polymeric molecular weight of 500 to 1,000,000, and $X^-$ is a halide ion,

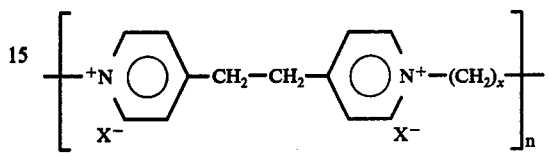
V $x = 6-10$, $n$ is the number of repeating monomeric groups and is selected so as to give a polymeric molecular weight of 500 to 1,000,000, and $X^-$ is a halide ion,

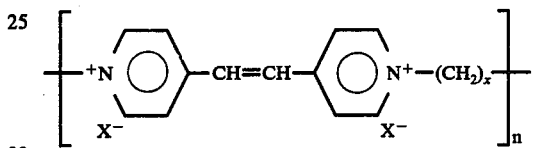
VI $x = 6-10$, $n$ is the number of repeating monomeric groups and is selected so as to give a polymeric molecular weight of 500 to 1,000,000, and $X^-$ is a halide ion,

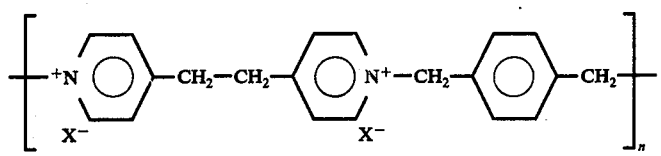
VII $n$ is the number of repeating monomeric groups and is selected so as to give a polymeric molecular weight of 500 to 1,000,000, and $X^-$ is a halide ion,

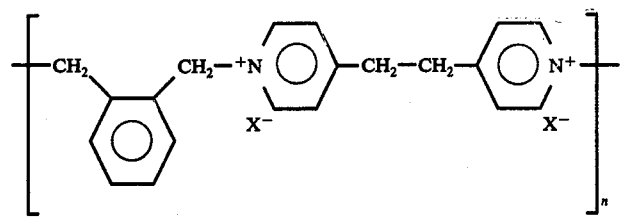
VIII $n$ is the number of repeating monomeric groups and is selected so as to give a polymeric molecular weight of 500 to 1,000,000, and $X^-$ is a halide ion,

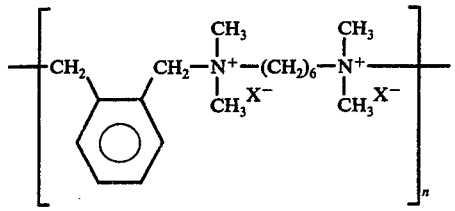

IX $n$ is the number of repeating monomeric groups and is selected so as to give a polymeric molecular weight of 500 to 1,000,000, and $X^-$ is a halide ion.

Another preferred polymer is polyoxyethylene (dimethylamino) ethylene (dimethylamino) dichloride. This polymer, supplied by the Buckman Corporation of Memphis, Tennessee and called "Busan-77" has the following structure:

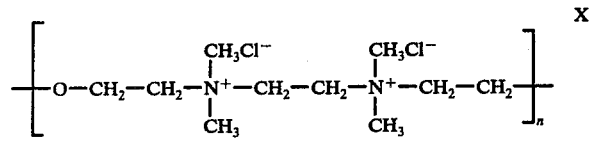

X wherein $n$ is an integer varying from 4 to 40, the average molecular weight is generally between 1,000 and 10,000, and the cationic charge density is 0.0106.

The polymer with Formula I above can be prepared by techniques well known in the art of quaternizing acrylic or methacrylic acid polymers. Such a method is exemplified later herein.

Formulas II, III and IV-IX can be prepared by methods described in *Polymer Letters*, A. Rembaum et al., Vol. 6, p. 160 (1968), Vol. 7, p. 383 (1969), Vol. 8, p. 457 (1970), incorporated herein by reference. These polymers are known as "ionenes" which name has been accepted by the editors of Chemical Abstracts. The reaction to form a polymer of formula III, which reaction is similar for those required to form polymers of structures II and IV-IX, is as follows:

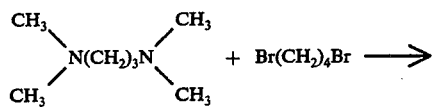

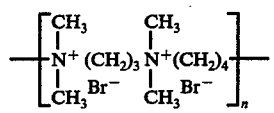

where $n$ is the number of repeating monomeric groups and is selected so as to give a polymeric molecular weight of from about 500 to about 1,000,000.

The above reaction can be carried out at room temperature in a number of solvents, e.g., dimethyl sulfoxide, methanol, benzene, dimethyl formamide, dimethyl formamide-water mixtures, and various combinations of the above. The yield with the above reaction is greater than 90% and the molecular weight can be varied by varying the concentration of the reactants, but generally is in the range of about 10,000 to about 40,000.

The polymer with formula X above is disclosed in U.S. Pat. No. 3,771,989, Pera et al., Nov. 13, 1973, incorporated herein by reference. The polymer is made by reacting N,N,N',N'-tetramethylethylene diamine with dichloroethyl ether in an aqueous solution.

The coating of the abrasive is carried out by contacting the hard mineral abrasive with an aqueous solution of the cationic polymer, and is preferentially carried out prior to the addition of cationic therapeutic ingredients to the dentifrice compositions.

The coating treatment, in order to be effective, should be carried out for a sufficient length of time to provide an opportunity for the cationic polymer to coat substantially the entire surface of the hard mineral substance. A period of at least about 5 minutes is perferred and a period of abut 20 minutes is most preferred.

The amount of cationic coating material which is deposited on the hard mineral abrasive can vary from about 2% to about 25% by weight of the uncoated abrasive, and preferably from about 3% to about 15%. The amount which is deposited can be varied by the concentration of cationic polymer in the solution used fo the coating treatment, and by the length of time of the treatment. Generally, the concentration of cationic polymer in the coating treatment solution is from about 3% to about 35%.

Any cationic therapeutic agent can be used in combination with the coated abrasives of this invention and will have improved compatibility with the abrasive (i.e., will be less reactive toward the abrasive) compared to the situation wherein they are used with an abrasive which is not coated in accordance with the present invention. Cationic therapeutic agents include such things as cationic anitbacterial agents and the water-soluble salts of certain metallic cations. Preferred cationic antibacterial agents are the bis-biguanide compounds which are known as effective antiplaque agents which demonstrate anticaries activity. Such bis-biguanide compounds are known, having been disclosed in U.S. Pat. No. 2,684,924, Rose et al., July 27, 1954; U.S. Pat. No. 2,990,425, Senior et al., June 27, 1961; U.S. Pat. No. 2,830,006, Burtwell et al., Apr. 8, 1958; and U.S. Pat. No. 2,863,019, Burtwell et al., Dec. 9, 1958.

This bis-biguanide compounds which are suitable for use in this invention have the generic formula:

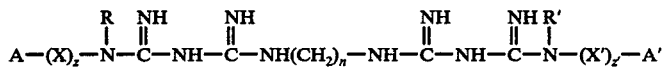

wherein A and A' each represent either (1) a phenyl radical which optionally is substituted by an alkyl or alkoxy group containing from 1 to about 4 carbon stoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein $z$ and $z'$ each can be either 0 or 1; wherein R and R' each represent either hydrogen, an alkyl radical containing from 1 to about 12 carbon atoms, or an aralkyl radical containing from 7 to about 12 carbon atoms; wherein $n$ is an integer from 2 to 12 inclusive; and wherein the polymethylene chain $(CH_2)_n$ may optionally be interrupted by oxygen or sulfur atoms, aromatic nuclei, etc. The pharmaceutically acceptable salts of the above compounds are especially desirable. Water-soluble salts include the acetate, the hydrochloride, and especially the gluconate salt of the above compounds. Water-insoluble salts are disclosed in the abandoned application of John William Haefele, Ser. No. 338,464, filed Mar. 6, 1973, incorporated herein by reference, said application being a continuation-in-part of application Ser. No. 267,816, filed June 30, 1972, now abandoned, the disclosure of which application is now incorporated into U.S. Pat. No. 4,025,616, issued May 24, 1977. A preferred bis-biguanide compound is 1,6-di($N_1,N_1'$-p-chlorophenyldiguanido-$N_5$, $N_5'$)hexane and its pharmaceutically acceptable salts. Specific examples of these and other bis-biguanide compounds are disclosed hereinafter.

The bis-biguanide compounds are normally used in amounts of from about 0.01 to about 2.5% by weight of the dentifrice composition herein, preferably from about 0.05 to about 1.2%, and most preferably from about 0.1 to about 0.8%. Depending upon the composition, lesser or greater amounts may be used. In general, all that is required is to have an effective amount of the bis-biguanide salt in the mouth sufficient to give anti-plaque and/or anitcaries effectiveness.

Specific examples of water-soluble bis-biguanide compounds are 1,6-di($N_1,N_1'$-p-chlorophenyldiguanido-$N_5,N_5'$)-hexane digluconate; 1,6-bis-(2-ethylhexyl-biguanidohexane)dihydrochloride; 1,6-di-($N_1,N_1'$-phenyldiguanido-$N_5,N_5'$)-hexane tetrahydrochloride; 1,6-di($N_1,N_1'$-phenyl-$N_1,N_1'$-methyldiguanido-$N_5,N_5'$)-hexane dihydrochloride; 1,6-di($N_1,N_1'$-o-chlorophenyl-diguanido-$N_5,N_5'$)hexane dihydrochloride; 1,6-di($N_1,N_1'$-2,6-dichlorophenyldiguanido-$N_5,N_5'$)hexane dihydrochloride; 1,6-di[$N_1,N_1'$-β-(p-methoxyphenyl)-diguanido-$N_5$, $N_5'$]-hexane dihydrochloride; 1,6-di($N_1,N_1'$-α-methyl-β-phenyldiguanido-$N_5,N_5'$)hexane dihydrochloride; 1.6-di($N_1,N_1'$-p-nitrophenyldiguanido-$N_5,N_5'$)hexane dihydrochloride; ω: ω'-di($N_1,N_1'$-phenyl-diguanido-$N_5,N_5'$)di-n-propylether dihydrochloride; ω: ω'-di($N_1,N_1'$-p-chlorophenyldiguanido-$N_5,N_5'$)-di-n-propylether tetrahydrochloride; 1,6-di($N_1,N_1'$-2,4-dichlorophenyldiguanido-$N_5,N_5'$)hexane tetrahydrochloride; 1,6-di($N_1,N_1'$-p-methylphenyldiguanido-$N_5,N_5'$)hexane dihydrochloride; 1,6-di($N_1,N_1'$-2,4,5-trichlorophenyldiguanido-$N_5,N_5'$)hexane tetrahydrochloride; 1,6-di[$N_1,N_1'$-α-(p-chlorophenyl)ethyldiguanido-$N_5,N_5'$]hexane dihydrochloride; ω: ω'-di($N_1,N_1'$-p-chlorophenyldiguanido-$N_5,N_5'$)m-xylene di-hydrochloride; 1,12-di-($N_1,N_1'$-p-chlorophenyldiguanido-$N_5,N_5'$)dodecane dihydrochloride; 1,10-di($N_1,N_1'$-phenyldiguanido-$N_5,N_5'$)decane tetrahydrochloride; 1,12-di($N_1,N_1'$-phenyldiguanido-$N_5,N_5'$)dodecane tetrahydrochloride; 1,6-di ($N_1,N_1'$-o-chlorophenyl-diguanido-$N_5,N_5'$)hexane dihydrochloride; 1,6-di($N_1,N_1'$-p-chlorophenyldiguanido-$N_5,N_5'$)hexane tetrahydrochloride; ethylene bis (1-tolyl biguanide); ethylene bis(p-tolyl biguanide); ethylene bis (3,5-dimethylphenyl biguanide); ethylene bis(p-tert-amylphenyl biguanide); ethylene bis(nonylphenyl biguanide); ethylene bis(phenyl biguanide); ethylene bis(N-butylphenyl biguanide); ethylene bis (2,5-diethoxyphenyl biguanide); ethylene bis (2,4-dimethylphenyl biguanide); ethylene bis(o-diphenyl biguanide); ethylene bis(mixed amyl naphthyl biguanide); N-butyl ethylene bis(phenyl biguanide); trimethylene bis(o-tolyl biguanide); N-butyl trimethylene bis(phenylbiguanide); tetramethylene bis(1-tolyl biguanide); the specific compounds disclosed in U.S. Pat. No. 2,863,919, Birtwell et al., (Dec. 9, 1958), said patent being incorporated herein by reference; the specific compounds disclosed in U.S. Pat. No. 3,468,898, Cutler et at., (Sept. 23, 1969), said patent being incorporated herein by reference.

Pharmaceutically acceptable water-insoluble salts of bis-biguanide compounds are useful in the compositions of the current invention to reduce the staining of the pellicle film caused by the extended use of the bis-biguanide compounds. These water-insoluble salts are formed by the reaction of the bis-biguanide with certain salt forming anions. Many such water-insoluble salts are disclosed in the abandoned application of John William Haefele, Ser. No. 338,464, filed Mar. 6, 1973, the disclosure of which application is now incorporated into U.S. Pat. No. 4,025,616, issued May 24, 1977. Included among the anions which will form pharmaceutically acceptable water-insoluble salts are bisulfite, polymaleate, N-coconut-alkyl sarcosinate, phosphite, hypophosphite, perfluorooctanoate, silicate, sorbate, salicylate, maleate, tartrate, citrate, fumarate, ethylenediamine tetraacetate, iminodiacetate, cinnamate, thiocyanate, arginate, pyromellitate, tetracarboxy butyrate, benzoate, glutarate, monofluorophosphate, perfluoropropionate, and anions derived from phosphorous anticalculus agents such as ethane-1-hydroxy-1,1-diphosphonic acid (EHDP).

The therapeutically active metallic cations whose water-soluble salts may be used in compositions of the present invention can be any metallic cation which can help reduce the susceptibility of tooth enamel to develop caries. Examples of acceptable therapeutically active cations are stannous, indium, calcium, strontium, antimony, molybdenum, titanium, and gold. Typical suitable salts of these cations are the halides, nitrates and sulfates, e.g., stannous fluoride, indium fluoride, calcium chloride, strontium chloride, antimony trifluoride, molybdenum hexafluoride, titanium tetrafluoride and auric chloride. The amount of the water-soluble salts of the therapeutically active metallic cations may be present at a level of from about 0.05 to about 2.5%, preferably from about 0.05 to about 1.5%.

The coated abrasive may be from about 4 to about 95% of the dentifrice composition. However, it is preferred that in toothpastes the coated abrasive be from about 6 to about 60% by weight of the dentifrice composition, and in toothpowders, the coated abrasive be from about 20 to about 95% of the dentifrice composition. The dentifrice compositions comprise, in addition to the coated abrasive, an effective amount of the cationic therapeutic agents mentioned hereinbefore.

The dentifrice of this invention may also contain one or more other optional ingredients well known for use in toothpastes and toothpowders. Without limitation, these include the following: Water; soaps and synthetic detergents, e.g., water-soluble soaps of $C_{12}-C_{18}$ fatty acids, water-soluble alkyl and alkyl ether sulfates and sulfonates having alkyl groups with 8 to 18 carbon atoms, water-soluble salts of sulfonated monoglycerides of fatty acids having from 10 to 18 carbon atoms, water-soluble salts of sulfated fatty alcohols having from 10 to 18 carbon atoms, salts of fatty acid amides of taurines, such as sodium-N-methyl-N-palmitoyl tauride, salts of fatty acid esters of isethionic acid, and substantially saturated aliphatic acyl amides of saturated aliphatic monoamino carboxylic acids having 2 to 6 carbon atoms and in which the acyl radical contains 12 to 16 carbon atoms, such as sodium N-lauroyl sarcoside; flavoring agents; oxygen-releasers, e.g., perborate; buffers, e.g., acetic acid, sweeteners, e.g., saccharin; humectants, preservatives; coloring materials, carriers and softeners, e.g., glycerine, sorbitol, ethyl alcohol, mineral oil, syrup, glycose, invert sugars, glycols and honey; and binders, e.g., gum tragacanth, sodium carboxymethylcellulose, hydroxyethylcellulose, xanthan gum, Irish moss, carragheen, starch, acacia gums, agar-agar, locust bean gum, pectin, polyalkylene glycols, polyalkylenes, silica aerogels, and petrolatum. The aforementioned optional ingredients in the dentifrice may be incorporated in the following ranges: about 0 to 70% carriers and softeners; about 0 to 30% binders; about 0 to 5% flavoring agents; about 0 to 60% water; about 0 to 10% buffers; about 0 to 2% preservatives; and about 0 to 6% soaps and synthetic detergents as surface tension depressants.

The dentifrice of this invention may be prepared by any suitable method. In general, the dentifrice may be formed by blending together the aforementioned ingredients, preferably coating the abrasive with the cationic polymer prior to the addition of the cationic agent. The pH of the dentifrice is preferably between 4 and 10.

The examples included below are submitted to illustrate, but not limit, this invention.

The percentages listed hereinbefore in the specification and hereinafter in the examples and the claims are by weight unless otherwise specified.

EXAMPLE I

Preparation of quaternized polydimethyl aminoethyl methacrylate was carried out in the following manner:

50 Grams of dimethylamino ethylmethacrylate monomer were mixed with 0.40 gram of 2,2'-azo bis-2-methylpropyl nitrile in 170 milliliters of absolute ethanol. The solution was refluxed for 11 hours, at which time it was very viscous. Methyl iodide in an amount 50% in excess of the amount required for quaternization, 67.8 grams, was added dropwise to the solution. The quaternized polymer was filtered out and washed with absolute ethanol.

EXAMPLE II

The reaction of Example I was conducted with a reflux time of 8.5 hours and an excess of methyl iodide of 10% (i.e., the total amount of methyl iodide was 49.7 grams).

EXAMPLE III

Dentifrice compositions were made using the following formula:

| Component | Grams |
|---|---|
| Abrasive * | 10.0 |
| Sorbitol | 12.5 |
| Glycerine | 7.5 |
| $H_2O$ | 158.5 |
| Busan 77 - polymer supplied by the Buckman Corp. defined hereinbefore | 1.4 |
| 20% solution chlorhexidine [1,6-di-($N_1,N_1'$-p-chlorophenyldiguanido-$N_5,N_5'$)-hexane] digluconate | 1.28 |

* The abrasives tested were as follows:
A - precipitated silica supplied by J. M. Huber Corp.
B - calcium pyrophosphate
C - calcium carbonate
D - Syloid 63 supplied by Davison Chemical Division, W. R. Grace & Co.
E - Syloid 74 supplied by Davison Chemical Division, W. R. Grace & Co.

Compositions identical to those shown above except that no Busan 77 was present were also made as were compositions with no Busan 77 present but with 2.36 grams of a 20% chlorhexidine digluconate/water solution. In the compositions containing Busan 77, the abrasive, sorbitol, glycerine, water and Busan 77 were mixed together first for 20 minutes and the chlorhexidine digluconate was then added. In the compositions containing no Busan 77, the same procedure was followed, except for the omission of Busan 77.

The samples were placed at either 80° or 120° F. for a period of days (the time period is shown in the following table) after which time the compositions were centrifuged and the supernatant was spectrophotometrically analyzed to determine the amount of chlorhexidine digluconate still in solution.

| Abrasive | | Relative % Chlorhexidine Remaining in Solution | | | |
|---|---|---|---|---|---|
| | | 3 days 80° F. | 12 days 80° F. | 4 days 120° F. | 14 days 120° F. |
| A + Busan 77 + | 1.28 g. 20% chlorhexidine soln. | 102* | 105 | 105 | 100 |
| A | 1.28 g. 20% chlorhexidine soln. | 55 | 51 | 51 | 47 |
| A | 2.36 g. 20% chlorhexidine soln. | 64 | 74 | 81 | 63 |
| B + Busan 77 + | 1.28 g. 20% chlorhexidine soln. | 100 | 104 | 104 | 100 |
| B | 1.28 g. 20% chlorhexidine soln. | 55 | 66 | 72 | 75 |
| B | 2.36 g. 20% chlorhexidine soln. | 74 | 77 | 84 | 80 |
| C + Busan 77 + | 1.28 g. 20% chlorhexidine soln. | 102 | 100 | 102 | 100 |
| C | 1.28 g. 20% chlorhexidine soln. | 36 | 33 | 33 | 33 |
| C | 2.36 g. 20% chlorhexidine soln. | 63 | 63 | 63 | 55 |
| D + Busan 77 + | 1.28 g. 20% chlorhexidine soln. | 93 | 102 | 100 | 100 |
| D | 1.28 g. 20% chlorhexidine soln. | 55 | 68 | 68 | 68 |
| D | 2.36 g. 20% chlorhexidine soln. | 74 | 74 | 74 | 74 |
| E + Busan 77 + | 1.28 g. 20% chlorhexidine soln. | 102 | 105 | 102 | 102 |
| E | 1.28 g. 20% chlorhexidine soln. | 7 | 7 | 7 | 3 |
| E | 2.36 g. 20% chlorhexidine soln. | 31 | 28 | 21 | 15 |

*Values are sometimes greater than 100% due to experimental error.

What is claimed is:
1. A coated abrasive composition consisting essentially of:
(A) A hard mineral substance having a hardness on the Mohs' scale of 2 or more and a particle size of from about 1 to about 30 microns; and as a coating for said hard mineral substance,
(B) from about 2 to about 25% by weight, based on the weight of said hard mineral substance, of a cationic water-soluble polymer having a cationic charge density of at least 0.003 and a molecular weight of from about 500 to about 1,000,000, said polymer being selected from the group consisting of:
(a) polyacryloxyalkyl ammonium salts;
(b) polymethacryloxyalkyl ammonium salts;
(c) polyacryloamido alkyl ammonium salts;
(d) polyalkenyl ammonium salts;
(e) polyvinyloxy ammonium salts;
(f) polyvinylbenzyl ammonium salts;

(g) polydiallyl ammonium salts;
(h) polyvinyl pyridinium ammonium salts;
(i) polyvinylimidazolium salts;
(j) polyalkylation quaternaries; and
(k) poly condensation quaternaries.

2. The composition of claim 1 wherein the amount of said cationic water-soluble polymer is from about 3 to about 15% by weight, based on the weight of said hard mineral substance.

3. The composition of claim 2 wherein the hard mineral substance is selected from the group consisting of:
(A) silica;
(B) calcium silicate;
(C) silicon carbide;
(D) alumina;
(E) ilmenite;
(F) hematite;
(G) zirconium silicate;
(H) calcium pyrophosphate;
(I) calcium carbonate;
(J) tricalcium phosphate;
(K) dicalcium orthophosphate; and
(L) insoluble metaphosphate.

4. The composition of claim 3 wherein the hard mineral substance is an amorphous silica.

5. The composition of claim 4 wherein the hard mineral substance is a silica xerogel.

6. The composition of claim 3 wherein the cationic water-soluble polymer is selected from the group consisting of:

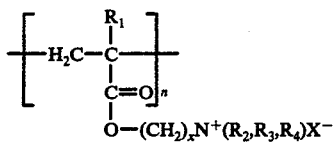
I where $n$ is the number of repeating monomeric groups and is selected so as to give a polymeric molecular weight of from 500 to 1,000,000, $R_1$ is either H or $CH_3$, $x$ is from 2 to about 5, $R_2$, $R_3$ and $R_4$ are the same or different alkyl radicals of from 1 to 4 carbon atoms or an aryl radical, and $X^-$ is a halide ion or $HSO_4^-$ or $CH_3SO_4^-$,

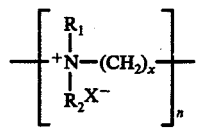
II where $x = 1$–14, $n$ is the number of repeating monomeric groups, and is selected so as to give a polymeric molecular weight of from 500 to 1,000,000, $R_1$ and $R_2$ are $CH_3$, and $X^-$ is a halide ion,

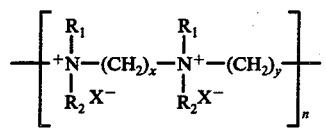
III where $x = 2$–6, $y = 3$–20, $n$ is the number of repeating monomeric groups and is selected so as to give a polymeric molecular weight of from 500 to 1,000,000, $R_1$ and $R_2$ are $CH_3$, and $X^-$ is a halide ion,

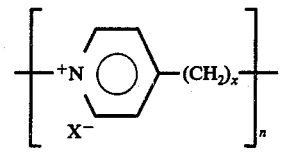
IV $x = 1$–12, $n$ is the number of repeating monomeric groups and is selected so as to give a polymeric molecular weight of 500 to 1,000,000, and $X^-$ is a halide ion,

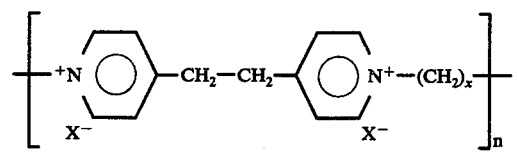
V $x = 6$–10, $n$ is the number of repeating monomeric groups and is selected so as to give a polymeric molecular weight of 500 to 1,000,000, and $X^-$ is a halide ion,

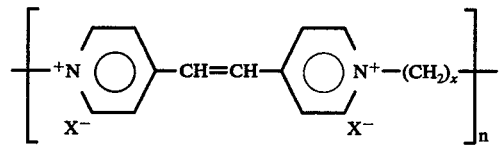
VI $x = 6$–10, $n$ is the number of repeating monomeric groups and is selected so as to give a polymeric molecular weight of 500 to 1,000,000, and $x^-$ is a halide ion,

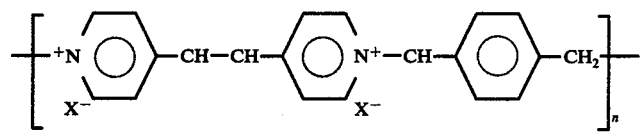
VII $n$ is the number of repeating monomeric groups and is selected so as to give a polymeric molecular weight of 500 to 1,000,000, and $X^-$ is a halide ion,

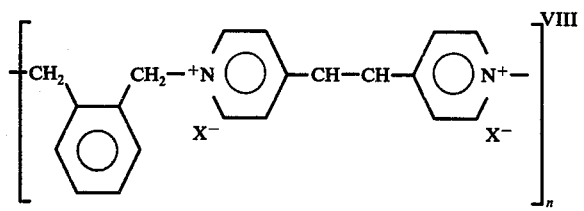
VIII $n$ is the number of repeating monomeric groups and is selected so as to give a polymeric molecular weight of 500 to 1,000,000, and $X^-$ is a halide ion,

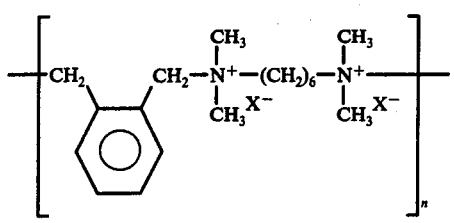

$n$ is the number of repeating monomeric groups and is selected so as to give a polymeric molecular weight of 500 to 1,000,000, and $X^-$ is a halide ion,

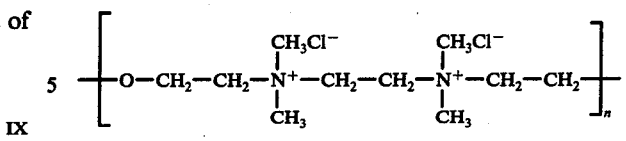

IX where $n$ is an integer varying from 4 to 40.

7. The composition of claim 4 wherein the cationic water-soluble polymer has the structure:

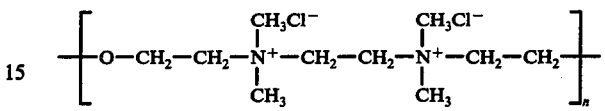

X where $n$ is an integer varying from 4 to 40.

* * * * *